United States Patent [19]

Blanchard et al.

[11] Patent Number: 4,797,554

[45] Date of Patent: Jan. 10, 1989

[54] ION MOBILITY SPECTROMETER

[75] Inventors: William C. Blanchard, Phoenix; Allan T. Bacon, Baltimore, both of Md.

[73] Assignee: Allied-Signal Inc., Morristown, N.J.

[21] Appl. No.: 137,700

[22] Filed: Dec. 24, 1987

[51] Int. Cl.$^4$ .............................................. H01J 49/40
[52] U.S. Cl. .................................... 250/287; 250/288; 250/282; 73/863.01
[58] Field of Search ................ 250/287, 288, 282; 73/863.01

[56] References Cited

U.S. PATENT DOCUMENTS

| 4,259,573 | 3/1981 | Prober et al. | 250/287 |
| 4,311,669 | 1/1982 | Spangler | 422/98 |
| 4,551,624 | 11/1985 | Spangler et al. | 250/287 |

Primary Examiner—Bruce C. Anderson
Assistant Examiner—Jack I. Berman
Attorney, Agent, or Firm—Robert M. Trepp; Bruce L. Lamb; Howard G. Massung

[57] ABSTRACT

An ion mobility spectrometer is described incorporating an air mixer having a clean air inlet and a sample air inlet, an ion mobility spectrometer cell for generating reaction ions and sample ions which are subsequently measured in a drift region, a first circuit for measuring the reactant ion peak and the sample ion peak, a second circuit for generating a feedback control signal to the air mixer in response to the reactant ion peak and a third circuit for generating a signal indicative of concentration of the sample molecules in sample air at the inlet utilizing the sample ion peak and the feedback control signal to the air mixer. The invention overcomes the problem of limited dynamic range due to saturation of the ion mobility spectrometer cell.

2 Claims, 3 Drawing Sheets

4,797,554

ION MOBILITY SPECTROMETER

GOVERNMENT CONTRACT

This invention was made with Government support under Contract F33615-86-4526 awarded by the U.S. Air Force. The Government has certain rights in this invention.

BACKGROUND OF THE INVENTION

1. Field of the Invention

This invention relates to Ion Mobility Spectrometers and more particularly to extending the dynamic range of the ion mobility spectrometer by using an input sample air mixer which is controlled by an electrical signal.

2. Description of the Prior Art

Present ion mobility spectrometers have limited dynamic range and are easily saturated when the sample molecules exceed the number of reaction ions available to ionize the sample molecules. Normal sensitivities of ion mobility spectrometers is in the range of parts per billion. An ionizer in the reaction region generates reactant ions over a period of time which in turn are attracted by the affinity of the sample molecule which removes charge from the reactant ions to itself. The ionized sample molecules are then detected by their drift time in a drift region. A typical range of concentrations of the sample is less than 100 to 1.

U.S. Pat. No. 4,259,573 which issued on Mar. 31, 1981 to J. M. Prober et al., describes an accurate method of determining small concentrations of chemical compounds by plasma chromatography "Ion Mobility Spectrometry". Small, known increments of species A plus, optionally, another calibrant species are introduced in turn into the plasma chromotograph together with the unknown sample chemical and the respective changes of the amplitude or area of a characteristic ion peak of species A in the unknown sample are measured.

U.S. Pat. No. 4,311,669 which issued on Jan. 19, 1982 to G. E. Spangler describes a sample inlet port of an ion mobility detector having a membrane interface. The sample which is included as a vapor component in a gas stream impinges on the exterior surface of the membrane and penetrates the membrane and is carried into the ion mobility spectrometer by means of a carrier gas which scrubs the interior surface of the membrane.

U.S. Pat. No. 4,551,624 which issued on Nov. 5, 1985 to G. E. Spangler et al. describes an ion mobility spectrometer system wherein a reagent such as acetone and/or carbon tetrachloride is injected into the carrier gas prior to entering the reaction region. The reagent has a higher proton affinity, electron affinity, or acidity than contaminants in the sample gas, a lower proton affinity, electron affinity, or acidity than at least 1 constituent of the sample gas to be detected, and does not cluster with water disposed in the reagent source.

SUMMARY OF THE INVENTION

A method and apparatus is described for detecting ions comprising an air mixer having a first input port for receiving clean air and a second input port for receiving sample air, the air mixer having a control input responsive to electrical signals for controlling the mixture of clean air received from the first input port to sample air received from the second input port, the air mixer having an output port coupled to the inlet of a reaction region, the reaction region including an ionization source for generating ions from the mixed clean air and sample air to form reactant ions and sample ions from selected sample molecules in the sample air, a shutter grid for introducing ions from the reaction region into the drift region having an electric field for drifting the ions towards a collector with circuitry attached for measuring the amplitude and mobility of the reaction ions and sample ions in the drift region, the circuitry including means for generating a first electrical signal indicative of the reaction ion amplitude, a second circuit for generating a second electrical signal from the first electrical signal indicative of a desired air mixture of clean air to sample air in response to the amplitude of the first electrical signal, the second electrical signal coupled to the control input of the air mixer, and a third circuit coupled to the first and second electrical signals for generating a third electrical signal indicative of the concentration of the sample molecule in the sample air at the second input port.

It is an object of the invention to extend the dynamic range of the ion mobility spectrometer by using at its input an air mixer with the ratio of sample air to clean air varied as a function of a selected output signal from the ion mobility spectrometer.

It is a further object of the invention to utilize an input sample air mixer to dilute the sample being measured to prevent the sample from saturating the output of the ion mobility spectrometer. The concentration of the chemical in the sample air that is being measured is then determined by the air mixer ratio and a selected output signal from the ion mobility spectrometer.

It is a further object of the invention to generate a feedback signal from the amplitude of the reactant ion output signal for diluting or premixing the input sample prior to entry into the ion mobility spectrometer.

DESCRIPTION OF THE PREFERRED EMBODIMENT

Figure 1:
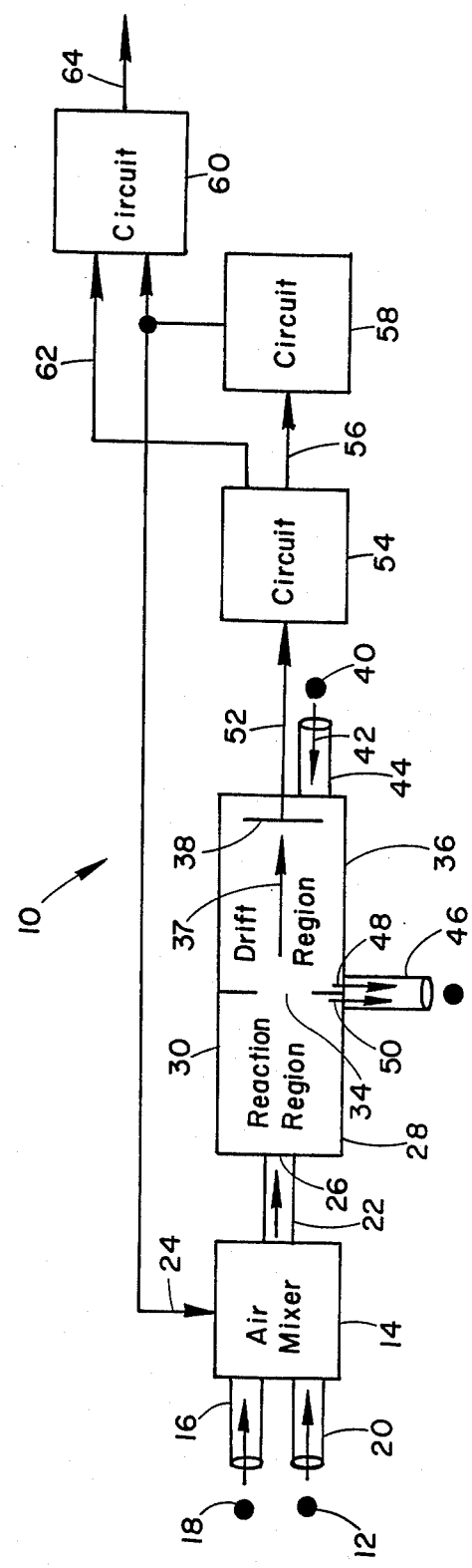
FIG. 1 is one embodiment of the invention.

Referring to FIG. 1, an ion mobility spectrometer for detecting ions such as sample ions from sample air 12. An air mixer 14 has a first input port 16 for receiving clean air 18. Clean air 18 may be air which has been scrubbed to be free of sample molecules or may be a gas such as nitrogen free of sample molecules. A second input port 20 receives sample air 12 which may contain sample molecules of a chemical of unknown concentration. Sample air 12 might be a gas such as nitrogen and the sample molecules. Air mixer 14 may have valves for controlling the flow of clean air 18 and sample air 12 into air mixer 14 which are mixed together therein and vented through output port 22. Air mixer 14 has a control input responsive to electrical signals over lead 24 for controlling the mixture of clean air received from input port 16 and sample air received from input port 20. Air mixer 14 has an output port 22 coupled to the inlet 26 of reaction region 28 of ion mobility spectrometer cell 30. Reaction region 28 includes an ionization source such as a nickle$^{63}$ which emits beta particles which ionizes the clean air 18 to provide reaction ions in reaction region 28. The reaction ions in turn ionize sample molecules which have a stronger affinity for the charge on the reaction ions. A shutter grid 34 allows sample ions and reaction ions to pass from reaction region 28 to drift region 36. The ions travel in direction shown by arrow 37 toward collector 38. Reaction region 28 may include means for generating an electric field therein to move the ions towards shutter grid 34. Drift region 36 may include means for generating an electric field therein to move the ions towards collector 38. One example of an ion mobility spectrometer cell 30 is described in U.S. Pat. No. 4,378,499 which issued on Mar. 29, 1983 to G. E. Spangler et al. entitled "Chemical Conversion For Ion Mobility Detectors Using Surface Interactions" which is incorporated herein by reference to show the construction details and operation of an ion mobility spectrometer cell.

Drift Gas 40 which may be for example dry nitorgen enters inlet 44 shown by arrow 42 into drift region 36 which exits vent 46 as shown by arrow 48. The clean air 18 and sample air 12 which enters inlet 26 of reaction region 28 is vented by vent 46 shown by arrow 50. The ions in the drift region 36 are collected by collector 38 and are neutralized. The neutralized molecules flow with the drift gas to vent 46.

The voltage on collector 38 is carried over lead 52 to an input of circuit 54. Circuit 54 provides a means for measuring the amplitude and drift time of reactant ions and sample ions reaching collector 38. Circuit 54 generates a first electrical signal indicative of the reactant ion amplitude which is coupled over lead 56 to an input of circuit 58. Circuit 58 functions to generate a second electrical signal on lead 24 from the first electrical signal on lead 56 indicative of a desired air mixture in air mixer 14 of clean air to sample air in response to the amplitude of the first electrical signal. The second electrical signal from circuit 58 is coupled over lead 24 to the control input of air mixture 14 and to an input of circuit 60. Circuit 54 also generates a third electrical signal indicative of the sample ion amplitude which is coupled over lead 62 to an input of circuit 60. Circuit 60 functions to generate a fourth electrical signal on lead 64 indicative of the concentration of the sample molecules in sample air 12. Circuit 60 functions to combine mathematically the third electrical signal indicative of amplitude of the sample ion with the second electrical signal indicative of a desired air mixture to provide the fourth electrical signal.

Figure 2:
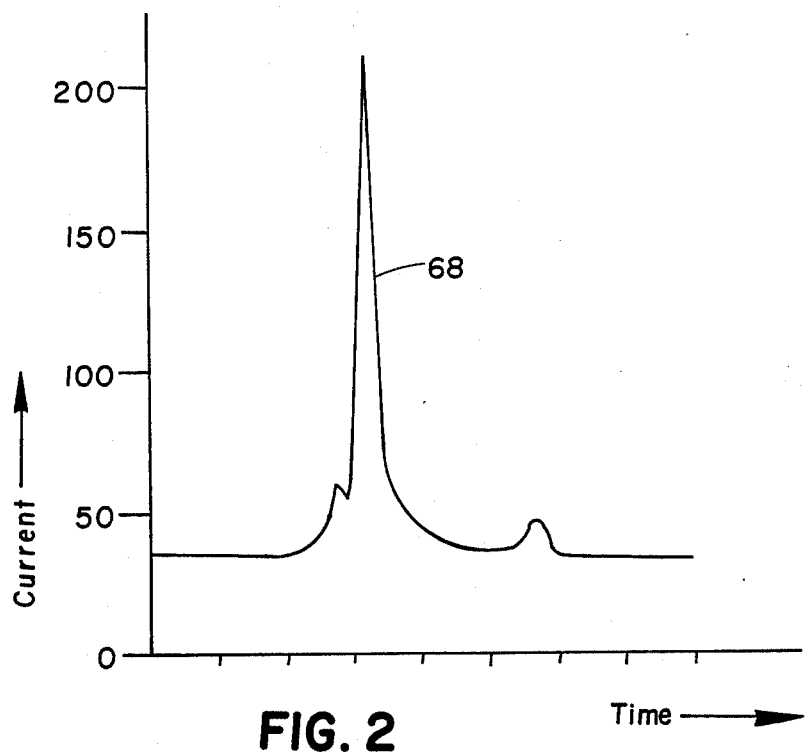
FIG. 2 is a graph of a reactant ion peak from an ion mobility spectrometer.

In operation of the ion mobility spectrometer 10, first clean air 18 was passed through air mixture 14 into reaction region 28 where reactant ions were generated and measured in drift region 36. FIG. 2 is a graph of the reactant ion peak shown by curve 68. In FIG. 2 the ordinant represents the response in units of current and the abscissa represents time. The electrical signal representative of the reactant ion peak shown by curve 68 would be provided on lead 52 to the input of circuit 58.

In clean air using water chemistry, reactant ions form in both positive and negative operating modes. The reactant ions are ionized clusters of water molecules and nitrogen as described by S. H. Kim et al. "Mobility Behavior and Composition of Hydrated Positive Reactant Ions in Plasma Chromotography with Nitrogen Carrier Gas" Anal.Chem.1978,50.

For the purposes of providing a test, an organic molecule methyl salicylate also known as oil of wintergreen was used as the sample molecule. Methyl salicylate is a much larger molecule than the reactant ions and has a lower mobility. Clean air 18 and sample air 12 containing methyl salicylate were mixed in air mixer 14 to provide a signature of 0.02 gamma which was passes into reaction region 28 wherein reactant ions were generated which in turn formed sample ions. The reactant ions and the sample ions were measured in drift region 36 and collected by collector 38.

Figure 3:
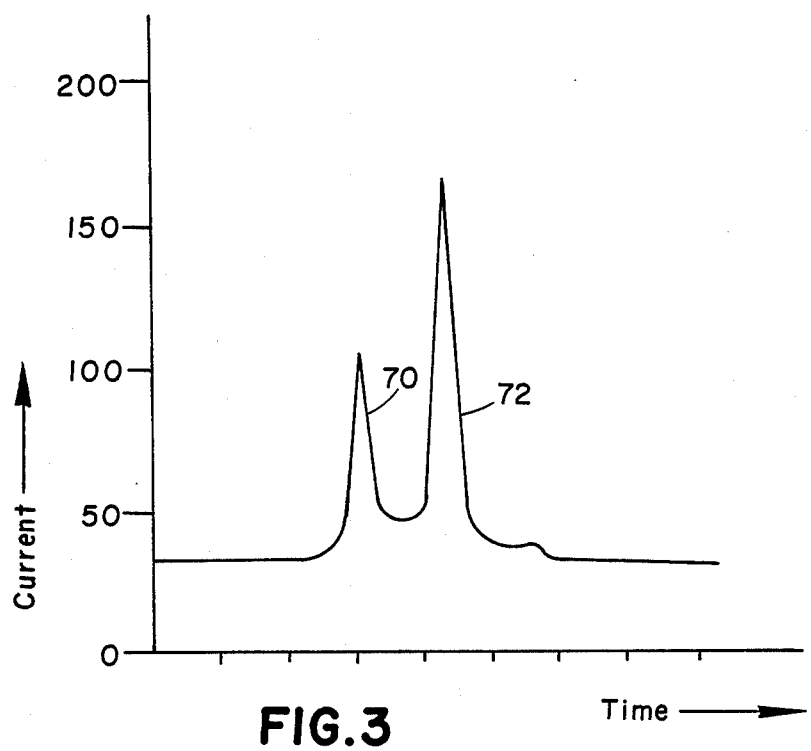
FIGS. 3–5 are graphs of the reactant ion peak and the sample ion peak from an ion mobility spectrometer.

FIG. 3 is a graph of the response of the signal on lead 52. Curve 70 shows the reactant ion peak and curve 72 shows the sample ion peak wherein the sample molecule is methyl salicylae. In FIG. 3 the ordinant represents amplitude in units of current and the abscissa represents time. Generally, the number of ions generated in a unit of time in reaction region 28 is constant and therefore a limited number of molecules will become ionized prior to entry into the drift region 36. Thus the reduction of the amplitude peak of the reactant ion shown by curve 70 compared to curve 68 in FIG. 2 is due to the fact that reactant ions lost charge to form sample ions shown by curve 72 in FIG. 3.

Figure 4:
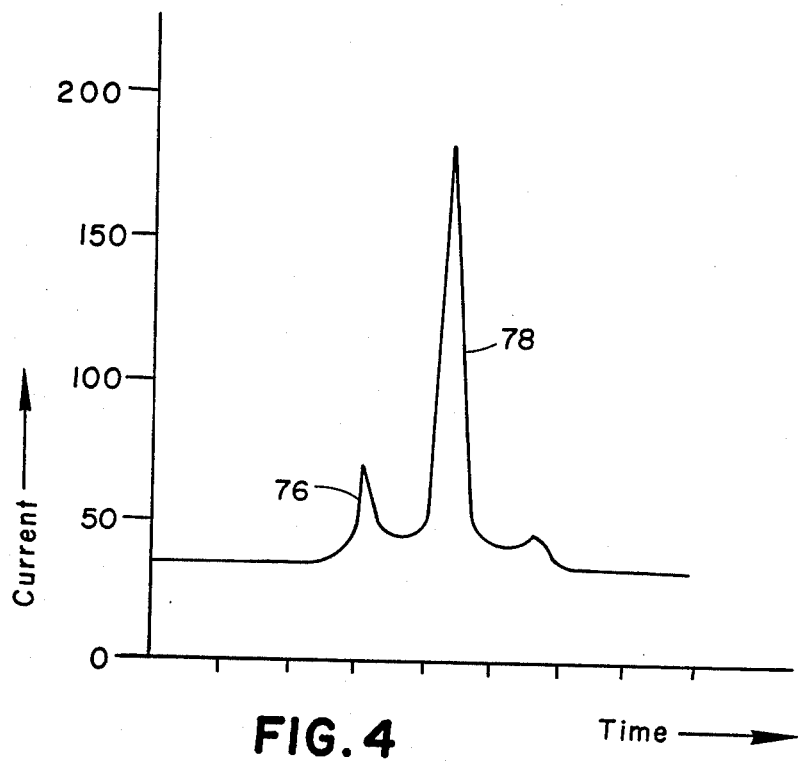

A further test was run wherein clean air 18 and sample air 12 was mixed in air mixer 14 to provide a concentration of methyl salicylate of 0.04 gamma which was passed into reaction region 28. The reactant ions and sample ions were measured in drift region 36 at collector 38. FIG. 4 shows the response of the electrical signal on lead 52. In FIG. 4 the ordinant represents amplitude in units of current and the abscissa represents time. The reactant ion peak is shown by curve 76 and the sample ion peak is shown by curve 78. It is noted that compared to FIG. 3 the reactant ion peak in FIG. 4 has diminished while the sample ion peak has increased.

Figure 5:
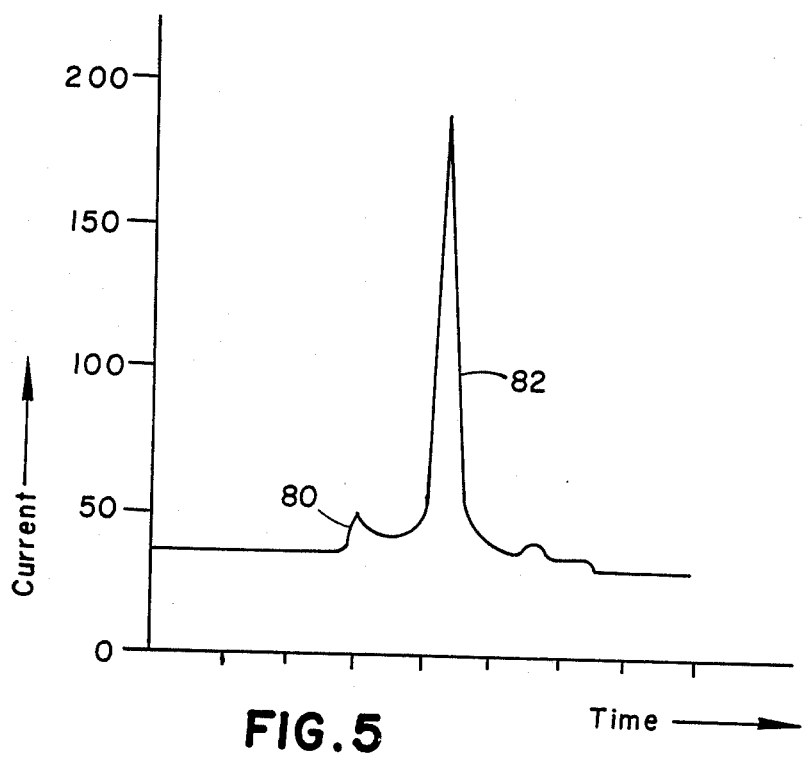

A further test was run wherein clean air 18 and sample air 12 was mixed in air mixer 14 to provide a concentration of methyl salicylate of 0.06 gamma which was passed into reaction region 28. The reactant ions and sample ions were measured in drift region 36 at collector 38. FIG. 5 shows a graph of the response on lead 52. In FIG. 5 the ordinant represents amplitude in units of current and the abscissa represents time. The reactant ion peak is shown by curve 80 and the sample ion peak is shown by curve 82. As compared to FIG. 4 the reactant ion peak 80 in FIG. 5 has diminished further while the sample ion peak has increased. At this point as shown in FIG. 5, very few reactant ions are left to be used to ionize sample molecules, therefore the ion mobility spectrometer cell 30 is very near saturation. Thus once the reactant ion peak disappears, presumably all reactant ions were used to ionize sample ions and additional sample molecules may be present which were not ionized due to the insufficiency of reactant ions. FIGS. 3 through 5 show that the total ion concentration of reactant ions and sample ions has remained essentially constant.

Circuit 58 functions to provide feedback via the second electrical signal to air mixer 14 to dilute sample air 12 with clean air 18 such that a constant reactant ion peak is observed by ion mobility spectrometer cell 30. The desired amount of reactant ion concentration may be shown for example in FIG. 4 wherein reactant ion peak curve 76 is shown. By maintaining a level or amplitude of the reactant ion in ion mobility spectrometer cell 30 saturation due to an excess concentration of sample molecules will be avoided or prevented. Circuit 60 functions to combine the sample ion peak such as curve 78 in FIG. 4 with the output signal of circuit 58 which controls the air mixer 14 to provide an output signal on lead 64 indicative of the concentration of the sample molecule such as methyl salicylate in sample air 12.

A method and apparatus has been described for diluting sample air 12 with clean air 18 to provide a concentration of sample air 12 to the ion mobility spectrometer cell 30 which will not saturate the cell. Saturation is prevented by circuit 54 which monitors the reactant ion peak, the first elctrical signal, and circuit 58 which generates a feedback signal, the second electrical signal, to maintain the reactant ion peak at a predetermined level. The feedback signal is coupled to an air mixer 14 at the inlet to provide a predetermined concentration of sample air 12 with respect to clean air 18 at the inlet 26 of ion mobility spectrometer cell 30. Circuit 60 provides an output signal, the third electrical signal, indicative of the concentration of the sample molecule in sample gas 12 by combining the output of circuit 54 which provides an indication of the sample ion peak and the output of circuit 58 which provides the control signal to air mixer 14.

The invention claimed is:

1. An ion mobility spectrometer comprising:
   an air mixer having a first input port for receiving clean air and a second input port for receiving sample air, said air mixer having a control input responsive to electrical signals for controlling the mixture of said clean air received from said first input port to said sample air received from said second input port,
   said air mixer having an output port coupled to the inlet of the reaction region, said reaction region including means for generating ions from said mixed clean air and sample air to form reactant ions and sample ions from selected sample molecules in said sample air,
   means for introducing said ions into a drift region,
   said drift region including means for measuring the amplitude and mobility of reactant ions and sample ions in said drift region,
   said means for measuring including means for generating a first electrical signal indicative of the reactant ion amplitude,
   first means for generating a second electrical signal from said first electrical signal indicative of a desired air mixture of said clean air to said sample air in response to the amplitude of said first electrical signal, said second electrical signal coupled to said control input of said air mixer, and
   second means coupled to said first and second electrical signals for generating a third electrical signal indicative of the concentration of said sample molecule in said sample air.

2. A method for operating an ion mobility spectrometer comprising the steps of:
   introducing a mixture of clean air and sample air into an ion mobility spectrometer cell,
   measuring the reactant ion peak,
   generating a control signal in response to the reactant ion peak which is coupled to the control input of an air mixer,
   mixing clean air and sample air in response to said control signal,
   passing the clean air and sample air which has been mixed into the reaction region of said ion mobility spectrometer cell,
   measuring the reactant ion peak,
   measuring the sample ion peak, and
   generating a signal indicative of a sample concentration of the sample air by mathematically combining the sample ion peak with said control signal.

* * * * *